US007387803B2

(12) United States Patent
Licari

(10) Patent No.: US 7,387,803 B2
(45) **Date of Patent: *Jun. 17, 2008**

(54) DIETARY FIBER DELIVERY SYSTEM

(75) Inventor: Jerome J. Licari, Plymouth, MN (US)

(73) Assignee: CNS, Inc., Minneapolis, MN (US)

(*) Notice: Subject to any disclaimer, the term of this patent is extended or adjusted under 35 U.S.C. 154(b) by 82 days.

This patent is subject to a terminal disclaimer.

(21) Appl. No.: 11/046,436

(22) Filed: Jan. 28, 2005

(65) Prior Publication Data

US 2005/0129758 A1 Jun. 16, 2005

Related U.S. Application Data

(60) Division of application No. 10/197,920, filed on Jul. 16, 2002, now Pat. No. 6,982,093, which is a continuation of application No. 08/771,960, filed on Dec. 23, 1996, now Pat. No. 6,455,068.

(60) Provisional application No. 60/009,231, filed on Dec. 26, 1995.

(51) Int. Cl.
*A01N 65/00* (2006.01)
*A61K 36/45* (2006.01)

(52) U.S. Cl. ...................................................... 424/732

(58) Field of Classification Search ................. 424/732
See application file for complete search history.

(56) References Cited

U.S. PATENT DOCUMENTS

| | | | |
|---|---|---|---|
| 3,424,842 A | 1/1969 | Nürnberg | |
| 3,974,272 A | 8/1976 | Polli et al. | |
| 4,021,545 A | 5/1977 | Nair et al. | |
| 4,283,432 A | 8/1981 | Mitchell et al. | |
| 4,285,735 A | 8/1981 | Mitchell et al. | |
| 4,421,852 A | 12/1983 | Hoehn et al. | |
| 4,680,189 A | 7/1987 | Schumacher et al. | |
| 4,681,771 A | 7/1987 | Adachi et al. | |
| 4,724,136 A | 2/1988 | Scheibl | |
| 4,758,515 A | 7/1988 | Barwald et al. | |
| 4,778,676 A | 10/1988 | Yang et al. | |
| 4,824,672 A | 4/1989 | Day et al. | |
| 4,865,850 A | 9/1989 | Shell et al. | |
| 4,871,574 A | 10/1989 | Yamazaki et al. | |
| 4,877,627 A | 10/1989 | Leitz et al. | |
| 4,882,152 A | 11/1989 | Yang et al. | |
| 4,882,160 A | 11/1989 | Yang et al. | |
| 5,013,576 A | 5/1991 | Nakazawa et al. | |
| 5,051,408 A | 9/1991 | Cooper | |
| 5,085,883 A | 2/1992 | Garleb et al. | |
| 5,169,671 A | 12/1992 | Harada et al. | |
| 5,260,279 A | 11/1993 | Greenberg | |
| 5,281,415 A | 1/1994 | Suzuki et al. | |
| 5,292,518 A | 3/1994 | Kuhrts | |
| 5,312,626 A | 5/1994 | Gergely et al. | |
| 5,320,848 A | 6/1994 | Geyer et al. | |
| 5,342,631 A | 8/1994 | Yatka et al. | |
| 5,403,612 A | 4/1995 | Huang | |
| 5,422,346 A | 6/1995 | Mitchell et al. | |
| 5,425,961 A | 6/1995 | Yatka et al. | |
| 5,431,929 A | 7/1995 | Yatka et al. | |
| 5,444,054 A | 8/1995 | Garleb et al. | |
| 5,445,826 A | 8/1995 | Kuhrts | |
| 5,447,741 A | 9/1995 | Goldman | |
| 5,476,678 A | 12/1995 | Walter et al. | |
| 5,478,732 A | 12/1995 | Kunz et al. | |
| 5,501,858 A | 3/1996 | Fuisz | |
| 5,531,989 A * | 7/1996 | Paul | 424/93.4 |
| 5,550,113 A | 8/1996 | Mann | |
| 5,589,182 A | 12/1996 | Tashiro et al. | |
| 5,614,501 A | 3/1997 | Richards | |
| 5,721,345 A | 2/1998 | Roberfroid et al. | |
| 5,925,190 A | 7/1999 | Richards | |
| 5,958,457 A | 9/1999 | Santiago et al. | |
| 6,087,092 A | 7/2000 | Richards | |
| 6,241,983 B1 | 6/2001 | Paul et al. | |
| 6,461,643 B2 | 10/2002 | Milstein et al. | |
| 6,610,329 B2 | 8/2003 | Santiago et al. | |
| 6,716,454 B2 | 4/2004 | Meignant et al. | |
| 7,005,141 B2 | 2/2006 | Milstein et al. | |
| 2004/0062773 A1 | 4/2004 | Santiago et al. | |

FOREIGN PATENT DOCUMENTS

| | | |
|---|---|---|
| BE | 903926 | 4/1986 |
| DE | 4003140 | 8/1991 |
| EP | 0 367 724 B1 | 2/1993 |
| EP | 0 643 962 A1 | 3/1995 |
| EP | 96944880.2 | 4/2006 |
| FR | 2673360 | 9/1992 |
| HU | 203959 | 6/1991 |
| JP | 61231966 | 10/1986 |
| JP | 2276556 | 11/1990 |
| JP | 3280859 | 12/1991 |
| JP | 4311371 | 11/1992 |
| JP | 07069902 | 3/1995 |
| NO | 903542 | 2/1991 |
| WO | WO 93/02566 | 2/1993 |
| WO | WO 94/22327 | 10/1994 |
| WO | WO 95/26646 | 10/1995 |
| WO | WO 9602263 A1 | 2/1996 |
| WO | PCT/US96/20245 | 4/1997 |

OTHER PUBLICATIONS http://pharmlabs.unc.edu/lozenge/text.htm, 1996, p. 1-6.*

(Continued)

*Primary Examiner*—Jon Weber
*Assistant Examiner*—Tiffany Gough
(74) *Attorney, Agent, or Firm*—Dara L. Dinner; Theodore R. Furman; Charles M. Kinzig

(57) ABSTRACT

A delivery system and method for delivering soluble dietary fibers in a chewable tablet form which is palatable and demonstrates a high degree of consumer acceptability.

29 Claims, No Drawings

OTHER PUBLICATIONS

Shangraw, "Compressed Tablets by Direct Compression", *Pharmaceutical Dosage Form: Tablets.* vol. 1, 2nd ed., 1989, pp. 195-246, Marcel Dekker Inc., New York, New York.
Chalmers et al., "Oxytetracycline Tablet Formulations: Effect of Variations in Binder Concentration and Volume on Granule and Tablet Properties", *Journal of Pharmacy and Pharmacology*, Mar. 1976, pp. 228-233, vol. 28, No. 3.
Carstensen et al., Physical Aspects of Wet Granulations I: Distribution Kinetics of Water, *Journal of Pharmaceutical Sciences*, Jul. 1976, pp. 992-997, vol. 65, No. 7.
Schlossman et al., "The Evaluation of Chemical Binders and Their Effect on Pressed Powders", *Journal of the Society of Cosmetic Chemists*, May 23, 1973, pp. 357-362, vol. 24.
Kristensen et al., "Granulation: A Review on Pharmaceutical Wet-Granulation", *Drug Development and Industrial Pharmacy*, vol. 13, 1987, pp. 803-872.
Channer et al., "The Effect of Size and Shape of Tablets on Their Esophageal Transit", *Journal of Clinical Pharmacology*, Feb. 1986, pp. 141-146, vol. 26, No. 2.
Overdahl et al., "Acute Occlusion of a Mainstem Bronchus by a Rapidly Expanding Foreign Body", *Chest*, May 1994, pp. 1600-1602, vol. 105.
"Shelf Busters," Drug Topics, Jan. 25, 1993, pp. 34-39.
"Maalox, Mylanta, Challenge P&G's Metamucil Laxative," Advertising Age, Jun. 21, 1993, pp. 3,48.
"Laxative Brand Shares," Marketing Share Reporter, 1995, p. 173.
"Regularly Increasing," Supermarket News, Aug. 16, 1993, pp. 27-29.
"Demographics Boon to Laxatives,"Chain Drug Review, Jan. 3, 1994, pp. 32, 37.
"Competition Remains Stiff in Laxatives," Chain Drug Review, Aug. 15, 1994.
"Competition in Laxatives Intensifies," Chain Drug Review, Jan. 2, 1995.
"Seniors a Key to Strong Laxatives Sales," Drug Topics, Feb. 20, 1995, pp. 63-64.
"Laxative Category Still in Doldrums," Chain Drug Review, Aug. 14, 1995, p. 12.
"Private Label Dominates Laxatives," Chain Drug Review, Jan. 1, 1996.
MMR/IRI H&BA Report, Laxative Sales Ending Feb. 25, 1996.
"Productive, Not Popular," Supermarket Business, Sep. 1996, pp. 113-114, 116, 120.
MMR/IRI H&BA Report, Laxative Sales Ending Jun. 30, 1996.
"Laxative Market in Doldrums," Chain Drug Review, Aug. 12, 1996, p. 48.
"Laxatives Arena in Need of a Spark," Chain Drug Review, Jan. 6, 1997.
"Laxatives," Drug Topics, Mar. 3, 1997, p. 92.
MMR/IRI H&BA Report, Laxatives Sales Ending Mar. 2, 1997; May 1997.
MMR/IRI H&BA Report, Laxative Sales Ending Jul. 19, 1997.
"Laxative Category Remains in Doldrums," Chain Drug Review, Aug. 4, 1997, pp. 21, 74.
"Laxative Segment in Doldrums," Chain Drug Review, Jan. 5, 1998.
"Bolus Obstruction of Gut After Use of Hydrophillic Colloid Laxatives". Brit. Med. J. 1965;1:165-8.
"Distal Esophageal Obstruction Due to a Guar Gum Preparation (Cal-Ban 3000)." Southern Medical Journal 1992; 85(6):642-5.
"The Dark Side of Fiber" Geriatric Nursing 1991; Jan./Feb.: 43.
"Goodman and Gilman's The Parmacological Basis of Therapeutics," 1990; 8 edition: Chapter 38 Agents Affecting Gastrointestinal Water Flux and Motility Digestants, and Bile Acids: p. 914-932.
"Modern Nutrition in Health and Disease", 1994; 8 edition: Chapter 4 Dietary Fiber: 89, 97.
"Bulk-forming laxatives and antacids to carry new warnings", Mayo Clinic Health Letter 1994; Mar. 1994: 3.
FDA News Release; P90-39: Jul. 27, 1990.
FDA News Release; P90-50: Oct. 29, 1990.
Federal Register; 55 FR 45782: Oct. 30, 1990.
FDA News Release; P91-17: Aug. 7, 1991.
FDA News Release; T92-14: Mar. 18, 1992.
FDA News Release; P93-35: Aug. 26, 1993.
Federal Register: 58 FR 45194: Aug. 26, 1993.
"Innovate with Raftilose (R)", Orafti Active Food Ingredients, Mar. 1999.
"Technical Properties of Raftiline (R),", Orafti Active Food Ingredients, Jul. 1998.
On the Presence of Inulin and Oligofructose as Natural Ingredients in the Western Diet; Critical Reviews in Food Science and Nutrition, Van Loo et al., 35(6) pp. 525-552 (1995).
OesoPhageal Obstruction to to Hygroscopic Gum Laxative, the Lancet, Feb. 16, 1980, pp. 364-365.
Complete Obstruction of the Esophagus, etc., Hinkel, JAMA vol. 146 No. 12, Jul. 21, 1951, pp. 1129-1131.
Glucomanna Diet Tablets, The Medical Journal of Australia, Mar. 17, 1984, pp. 350.
Acute Esophageal Obstruction, etc., Jay A. Noble et al., Nov. 1984, pp. 800.
Esophageal Obstruction Caused by Cal-Ban Morse, et al., Gastroenterology 1990;98: pp. 805-807.
Glucomannan and Risk of Esophageal Obstruction, British Medical Journal, vol. 292, Mar. 1, 1986, pp. 591-592.
Glucomanna Diet Tablets, The Medical Journal of Australia, vol. 142, Feb. 4, 1985, p. 204.
Esophageal Obstruction with a Dietary Fiber Product, etc., Opper, et al., J Clin Gastroentrol 1990; 12(6): pp. 667-669.
Cellulose Diet Fiber Pills, Jones et al, Arch Otolaryngol Head Neck Surg, vol. 116, Sep. 1990, pp. 1091.
Esophageal and Small Bowel Obstruction, etc., Lewis, the American Journal of Gastroenterology, vol. 87, No. 10, 1992, pp. 1424-1428.
Small Bowel Obstruction, etc., The New England Journal of Medicine, vol. 320, No. 17, Apr. 27, 1989, pp. 1148-1149.
Small Bowel Obstruction from Bran Cereal, JAMA, vol. 263, No. 6, Feb. 9, 1990, pp. 813-814.
Warning: Feeding Animals Hydrophilic Fiber Sources, etc., Struthers, 1986, pp. 47-49.
Intestinal Obstruction From Cecal Bezoar, etc., McIvor et al., Nutrition, vol. 6, No. 1, Jan./Feb. 1990, pp. 115-117.
High-Fibre Problem, The Practioner, Mar. 8, 1990, pp. 206.
Health Effects of Oligosaccharides, Tomomatsu, Food Technology, Oct. 1994, pp. 61-65.
Health Benefits and Practical Assets of High-Fiber Diets, Anderson et al., AM J Clin Nutr, 1994; 59 (Supplement) pp. 1242s-1247s.
Dietary Fiber and Health, JAMA, Jul. 28, 1989, vol. 262, No. 4, pp. 542-546.
Safety and Benefits of Fructooligosaccharides, etc., Spigel et al., Food Technology, Jan. 1994, pp. 85-89.
Influence of Dietary Neosugar, etc., Williams et al., Microbial Ecology in Health and Disease, vol. 7, 1994, pp. 91-97.
"Application of Fructooligosaccharide to Confections," Shokuhin to Kagaku (Foods and Science), 1989, pp. 103-109, vol. 31, No. 3.
Lees, R. and Jackson, E.B., "Chapter 14: Tablets, Lozenges and Extruded Paste," Sugar Confectionery and Chocolate Manufacture, 1975, pp. 286-298, Chemical Publishing Co., Inc., New York, N.Y.
Jackson, E.B., "Chapter 12: Tablets, Lozenges and Sugar Panning," Sugar Confectionery Manufacture, 1990, pp. 236-257, Van Nostrand Reinhold, New York, N.Y.
"Technical Properties of Raftiline200 ," Jul. 1998, Orafti Active Food Ingredients.
Seibel, W., et al., "Ballaststoffkonzentrate," Lebensmitteltechnik, 1994, No. 4, pp. 14-16.
Teeuwen, H.W.A., et al., "Inuline: Een Natuurlijke Voedingsvezel Herontdekt," Voedingsmiddelentechnologie, Nov. 1992, No. 24, pp. 12-13, 15-16.
De Soete, J., "Inulin und Oligofruktose—Geschmacks- und Texturverbesserung aus Zichorien," Lebensmitteltechnik, 1995, Nos. 7-8, pp. 39-40.
Quemener, B., et al., "Determination of Inulin and Oligofructose in Food Products, and Integration in the AOAC Method for Measurement of Total Dietary Fibre," Lebensm.-Wiss. u-Technol., 1994, vol. 27, No. 2, pp. 125-132.

Roberfroid, M., et al., "The Biochemistry of Oligofructose, a Nondigestible Fiber: An Approach to Calculate its Caloric Value," Nutrition Reviews, May 1993, vol. 51, No. 5, pp. 137-146.
Korsatko, W., et al., "Entwicklung Kombinierter Inulin/p-Aminohippursaure (PAH) Retard-Implantationstabletten zur Bestimmung der Clearance an Wachen Ratten," Pharmazie, 1987, vol. 42, No. 5, pp. 324-327.
Neuwirth, I., et al., "Demonstration of Rapid Production of Lactic Acid in Oral Cavity," Proceedings of the Society for Experimental Biology and Medicine, 1940, vol. 45, pp. 464-467.
Tkachenko, A.M., et al., "Dispersity of Inulin and Physicomechanical Properties," Sakharnaya Promyshlennost, 1994, No. 2, p. 31.
Berghofer, E., et al., "Pilot-scale Production of Inulin from Chicory Roots and its Use in Foodstuffs," Studies in Plant Science, 1993, No. 3, pp. 77-84.
Brown, J., "Effects of Interrupting the Renin-Angiostensin System on Sodium Excretion in Man," Journal of Physiology, 1988, No. 395, pp. 17-40.
Coussement, P., "Raftilose und Raftiline: Eine Neue Generation von Ballaststoffen," Deutsche Milchwirtschaft, 1995, vol. 46, No. 19, pp. 1060-1062.
Dysseler, P., et al., "Inulin, an Alternative Dietary Fibre. Properties and Quantitative Analysis," European Journal of Clinical Nutrition, Oct. 1995, vol. 49, suppl. 3, pp. S145-S152.
Feldheim, W., "Ballaststoffreiche Lebensmittel als Light-Produkte—eine Alternative?," Ernahrung/Nutrition, 1994, vol. 18, No. 3, pp. 105-107.
Bing, F.C., "Dietary Fiber—In Historical Perspective," Journal of the American Dietetic Association, Nov. 1976, vol. 69, pp. 498-505.
Roberfroid, M., "Dietary Fiber, Inulin, and Oligofructose: A Review Comparing their Physiological Effects," Critical Reviews in Food Science and Nutrition, 1993, vol. 33, No. 2, pp. 103-148
Sadjak, A., et al., "The Suitability of a Combined Inulin/PAH Retard Tablet for Measuring Renal Functions in the Conscious Rat," Agents and Actions, 1988, vol. 24, No. 1/2, pp. 210-24.
Jouany, J.-P., et al., "Evolution Postprandiale de la Composition Glucidique des Corps Microbiens du Rumen en Fonction de la Nature des Glucides du Regime," Annales de Biologie Animale Biochimie Biophysique, 1972, vol. 12, No. 4 pp. 673-677.
Robinson, R.K., "The Potential of Inulin as a Functional Ingredient," British Food Journal, 1995, vol. 97, No. 4, pp. 30-32.
Murray, J., et al., "Controlled Release of Microquantities of Macromolecules," Cancer Drug Delivery. 1984, vol. 1, No. 2, pp. 119-123.
Bower, R.H., et al., "Early Enteral Administration of a Formula (Impact) Supplemented with Arginine, Nucleotides, and Fish Oil in Intensive Care Unit Patients . . . ," Critical Care Medicine, Mar. 1995, vol. 23, No. 3, pp. 436-449.
American Academy of Pediatrics—Committee on Nutrition, "Plant Fiber Intake in the Pediatric Diet," Pediatrics, Apr. 1981, vol. 67, No. 4, pp. 572-575.
Cummings, J.H., et al., et al., "Gastrointestinal Effects of Food Carbohydrate," American J. Clinical Nutrition, 1995, vol. 61(suppl), pp. 938S-945S.
Cerra, F.B., et al., "Improvement in Immune Fuction in ICU Patients by Enteral Nutrition Supplemented with Arginine, RNA, and Menhaden Oil Is Independent of Nitrogen Balance," Nutrition, May/Jun. 1991, vol. 7, No. 3, pp. 193-199.

* cited by examiner

DIETARY FIBER DELIVERY SYSTEM

This application is a divisional of U.S. patent application Ser. No. 10/197,920, filed Jul. 16, 2002, now U.S. Pat. No. 6,982,093, which is a continuation of U.S. patent application Ser. No. 08/771,960, filed Dec. 23, 1996, now U.S. Pat. No. 6,455,068, and which claims the benefit of U.S. Provisional Application No. 60/009,231 filed Dec. 26, 1995.

BACKGROUND OF THE INVENTION

1. Field of the Invention

The present invention relates generally to a delivery system for dietary fibers and more particularly to a delivery system for soluble dietary fiber supplements preferably in the form of a safe, chewable tablet, lozenge, wafer, cookie or the like which is comprised in part of a relatively low viscosity, non-gelling and organoleptically pleasing dietary fiber component.

2. Description of the Prior Art

Unlike other nutrients, dietary fiber is not a single substance, but is a term used to identify plant polysaccharides and lignins that are not hydrolyzed by the endogenous secretions of the human digestive system. Thus, they reach the colon intact. Plant components which make up dietary fiber include, among others: structural polysaccharides (cellulose and hemicellulose), nonstructural polysaccharides (pectines, B-glucans; gums and mucilages) and structural non-polysaccharides (lignin). Dietary fibers are commonly characterized by their water solubility and their relative susceptibility to microbial degradation into fermentable and nonfermentable fiber fractions. In general, pectines, gums and mucilages are water soluble, while lignin, cellulose and hemicellulose are water insoluble.

Dietary fibers by definition reach the colon intact and thus generally escape digestion and absorption in the small intestines; however, such fibers are susceptible to varying degrees of microbial fermentation or degradation in the colon. Such degradation results in the production of carbon dioxide, hydrogen, methane, and various short chain fatty acids.

For much of the twentieth century the common notion among clinicians and nutritionists was that fiber was roughage or the like comprised of indigestible cell walls. Except for providing bulk for normal bowel function, such fiber was considered to be of no nutritional value. Accordingly, many food scientists directed their efforts toward enhancing the purity of food by removing dietary fiber.

However, during the last few decades, stimulated principally by epidemiological observations revealing differences in disease patterns between populations, researchers began to accumulated a large body of evidence linking a low fiber western diet with the incidence of numerous chronic diseases. Numerous laboratory and clinical investigations have also confirmed various risk factors associated with low fiber diets and the protective nature of high fiber diets.

The association of high dietary fiber intake with lower risk or improvement in several chronic diseases has led to recommendations to increase dietary fiber consumption to 20-35 grams per day. Because of these recommendations and the mounting recognition of health benefits of high fiber diets, health care professionals have aggressively attempted to encourage individuals to consume high fiber diets that are rich in fruits, vegetables, legumes and whole grains. Regrettably, many of the most popular foods, and particularly those most popular in western diets, are low in dietary fiber. Thus, for those consuming an affluent "refined western diet", satisfying these recommendations is a difficult task. Accordingly, despite the recommendations advocating high fiber diets, the intake of dietary fiber has not significantly increased. Recent consumption surveys reveal that average dietary intake of fiber remains at approximately 10-12 grams per day.

As a result, a variety of dietary fiber supplements have been marketed for increasing the consumption of dietary fiber. Unfortunately, however, such supplements have achieved limited consumer acceptance. Much of the dissatisfaction arises because of the physical organoleptic and other characteristics of the fiber components which make up the great majority of dietary fiber supplements currently available. Common dietary fiber supplements are comprised of fiber components such as psyllium (sold under the trademark Metamucil or Fiberall), methylcellulose (sold under the trademark Citrucel) and polycarbophil or calcium polycarbophil (sold under the trademark Fiber Con). These generally have a significant affinity for water. Thus, when exposed to water or other fluids prior to or during ingestion, or when progressing through the digestive system, these components tend to swell quickly and produce highly viscous fluids and gels. For instance, when hydrated, psyllium fiber produces an unacceptably gummy, chewy product. This has led directly to increased safety risk such as choking, obstruction and the like, both during and after ingestion. In fact, scientific literature has reported obstructions (esophageal and small bowel) requiring medical attention from the consumption of both insoluble and soluble fiber supplements.

To minimize this problem, it is recommended that present fiber supplements be ingested while consuming a large quantity of liquids (a minimum of eight ounces of fluid) or that smaller quantities of the supplement be ingested. In fact, the FDA's Tentative Final Monograph for Laxatives specifies that a full glass (8 ounces) of liquid be taken with each dose of certain fiber supplements. Typically, dietary fiber supplements are ingested in the form of swallowable tablets, reconstitutable powders or wafers. Swallowable tablets, because of the above safety concerns, are limited to tablets of one gram or less and more typically 0.5 grams or less. This, however, leads to two areas of consumer dissatisfaction: the need to ingest a large amount of liquid per dose as well the need for a large number of doses to get a meaningful amount of fiber.

Fiber supplements in the form of a reconstitutable powder have also met with limited consumer acceptance due principally to mouth feel of the product (the texture and grittiness), gelling due to viscosity buildup, visual appearance, the relatively large amounts of liquid required for mixing and consumption and limited palatability. The inconvenience of reconstituting and ingesting the product outside the home and the necessity for cleanup also encumbers lifestyle and results in poor compliance. As an alternative, fibers supplements are often offered as wafers or as swallowable tablets as described above.

To overcome some of the problems identified above, the prior art teaches the encapsulation or pre-coating of dietary fiber supplements delivered as swallowable tablets. Although this somewhat improves certain of the organoleptic properties by masking undesirable flavors and texture and delays hydration until it passes through the oral cavity, the limitations resulting from the relatively small swallowable tablets continue to exist. The prior art also describes attempts to mask the fibrous mouth feel of current fiber supplements by concealing the dietary fiber in wafers, baked goods, granola-type products, power bars, cookies, cereals and snack foods. While this technology has achieved some degree of success, it often requires the inclusion of ingredients high in fat, carbohydrates and calories and low in dietary fiber. Thus, consumers wishing to restrict their caloric intake are often reluctant to utilize such products. Further, the level of dietary fiber that can be incorporated into other foods without adversely affecting the taste and mouth feel is quite limited. In general, the upper limit is about 5% by weight.

Still further, the prior art teaches the use of fine powders of dietary fibers, excipient and or dispersing agents to reduce the formation of fibrous clumps or "fish eyes" during rehydration. In comparison to coarser powders, the fine powders of dietary fibers tend to be less gritty upon reconstitution.

According, there is a need for a dietary fiber supplement which addresses the problems in the prior art and provides a dietary fiber supplement and a delivery system for a dietary fiber which does not pose safety concerns resulting from viscosity buildup or gelling and which is palatable, aesthetically pleasing and exhibits characteristics which enable it to be delivered as a chewable tablet or lozenge without the choking, obstruction or other safety concerns.

SUMMARY OF THE INVENTION

In contrast to the prior art, the present invention provides a dietary fiber supplement, and more particularly, a dietary fiber supplement delivery system which enables relatively large doses of fiber to be ingested with dissolution and substantial hydration in the oral cavity without experiencing safety concerns and while providing a palatable and organoleptically pleasing product. More specifically, the present invention relates to the discovery of a subset of soluble dietary fibers which do not significantly increase in viscosity or gel when exposed to water or other liquids, yet possess the desirable organoleptic characteristics and the ability to function as a dietary fiber. This particular subset of soluble dietary fibers exhibits characteristics which enable the same to be delivered as a chewable tablet, wafer or lozenge having excellent texture, mouth feel and palatability and which can be delivered without experiencing the choking, obstruction or other safety concerns commonly associated with dietary fiber supplements currently existing in the art. The dietary fiber supplement of the present invention is designed to be chewed or dissolved slowly and then swallowed without experiencing such safety concerns or unpleasant organoleptic or other properties.

Further, the dietary fiber supplement of the present invention is organoleptically pleasing and does not require the addition of masking agents or coating techniques to improve its taste and mouth feel. Further, it does not require delaying hydration until it passes out of the oral cavity as is required with some present supplements. Accordingly, this subset of materials results in improved consumer acceptance and compliance. This in turn encourages and enables the long term consumption of fiber supplements for those individuals who will benefit from such increase in fiber intake.

Preferably the dietary fiber supplement in accordance with the present invention is comprised of a subset or category of fiber supplements which, when exposed to water or other fluid, do not result in significant buildup of viscosity or gelling. These fiber components are sometimes referred to herein as "non-gelling low viscosity fiber components" or simply as "low viscosity fiber components". More specifically, the category of materials that are applicable to the present invention are those materials which when exposed to water or other liquid result in a solution which does not gel and exhibits a viscosity significantly less than the viscosity of similar solutions of currently available dietary fiber supplements. Such materials also preferably exhibit organoleptically pleasing properties and palatability. Although a variety of dietary fiber components may exhibit these properties, the preferred embodiment contemplates a dietary fiber component comprised of inulin or fructooligosacchaides (FOS) either individually or in combination. In accordance with the present invention, such component is delivered in a chewable form as a chewable tablet, lozenge, wafer, cookie or the like (hereinafter referred to as a "chewable tablet") ranging in size from one-half gram to as much as ten grams. Preferably the chewable tablet comprises at least 10% by weight of the dietary fiber component, more preferably, at least 30% by weight and most preferably at least 50% by weight.

The present invention also relates to a dietary fiber delivery method for a human subject which involves preparing a chewable tablet or wafer of the type described above and then chewing and swallowing the tablet. This may be accomplished with or without water.

Most significantly, the present invention provides a delivery system for fiber supplementation in a chewable form which can deliver large quantities of fiber, particularly in the range of 3-5 grams, in a single chewable tablet which unexpectedly is quite palatable and demonstrates a high degree of consumer acceptability. Notwithstanding the size of the chewable tablet or wafer, it provides a pleasing mouth feel which dissolves rapidly due to the presence of the soluble fiber used in this invention. The present invention thus avoids the unpleasant gritty or gummy textures associated with chewable fiber supplements of the prior art.

Accordingly, it is an object of the present invention to provide a novel, safe, advantageous, user friendly, convenient, highly acceptable mechanism for the delivery of dietary fibers in a form and in quantities previously unavailable.

Another object is to provide a chewable delivery system comprised of one or more soluble dietary fibers which are to be masticated (or slowly dissolved) in the oral cavity with substantial hydration and swallowed upon complete disintegration without experiencing the safety concerns and unpleasant organoleptic properties of presently available fiber supplements.

Another object of the present invention is to provide a chewable tablet for the administration of physiologically active soluble fibers or resistant starches while avoiding the safety concerns and other consumer disadvantages associated with such fibers.

Another object of the present invention is to provide a delivery system for a dietary fiber supplement which does not gel and which encourages long-term compliance and consumption.

A still further object of the present invention is to provide a dietary fiber supplement in a form which exhibits a relatively low viscosity when exposed to water or other liquids.

These and other objects of the present invention will become apparent with reference to the description of the preferred embodiment.

DESCRIPTION OF THE PREFERRED EMBODIMENT

Because of the association between high dietary fiber intake and improved health benefits, the general consensus and recommendations from health care professionals is to increase the consumption of dietary fiber. Because many diets, and in particular affluent western diets, fail to provide sufficient fiber intake, fiber supplements are highly recommended. Depending upon the particular individual's medical and health status and diet, it Is anticipated that the adult daily fiber supplement could range from 1-20 grams and more probably from 3-15 grams. Presently available fiber supplements are generally administered from 1-6 times per day in unit dosages of 0.5-3 grams.

In accordance with the present invention, a dietary fiber supplement delivery system is provided in which dramatically increased quantities of fiber supplements can be administered and ingested without danger of choking, internal obstruction or other safety concerns. Preferably, the system includes a chewable tablet comprised principally of a low viscosity dietary fiber component which when exposed to water or other liquid exhibits a relatively low viscosity (hereinafter sometimes referred to as "low viscosity fiber component"), but which still functions as a dietary fiber and provides highly desirable organoleptic and other properties.

The low viscosity fiber components useful in the present invention are those dietary fiber components which exhibit relatively low viscosity buildup when exposed to water or other fluids. More specifically, the dietary fiber components exhibiting the reduced viscosity property of the present invention are those fiber components which when combined with water to form a 10% by weight solution of the component exhibit a viscosity at 25.degree. C. which is preferably less than 100 centipoise (cps), more preferably less than 25 cps and most preferably less than cps.

Although it is contemplated that a variety of fiber components would meet this low viscosity requirement, the preferred embodiment contemplates that such component would be either inulin or a fructooligosaccharide (FOS). Inulin or FOS can be provided either individually or in combination and is preferably delivered as a chewable tablet. It can also be provided as a powder to be reconstituted with water, if desired. Inulin is comprised of fructofuranose polymers (oligomer and polymers of fructose) of varying chain lengths with a DP (degree of polymerization) ranging from 2 to 60 monomeric fructose units linked to a terminal glucose molecule. More preferably, inulin of the present invention has a DP of 2-20 and mostly preferably a DP of less than 10. FOS is a mixture of the smaller fructan polymer fractions with a DP of 2 to 8. Thus, the molecules of FOS have 2 to 8 fructose units linked to a terminal glucose molecule. FOS can be commercially produced by the partial enzymatic hydrolysis of inulin or enzymatically synthesized from sucrose. Inulin or FOS offer functional physical and organoleptic advantages over other nondigestible polysaccharides which make up what are currently considered as dietary fibers or resistant starches. These functional, organoleptic and aesthetic properties provide significant advantages to the present invention which do not exist with respect to present dietary fiber supplements. In contrast to currently available fiber supplements, inulin and FOS comprise relatively small polymers which at anticipated levels of fiber do not build viscosity, swell or gel. Additionally, inulin and FOS are slightly sweet and have a pleasing taste and texture.

The inulin material used in the practice of this invention may be obtained from a variety of commercially available sources. Economically obtainable amounts are found in a series of plants, such as Jerusalem artichoke tubers and dahlia tubers, and also in chicory roots. It is known to obtain inulin from these sources by hot water extraction and drying, see U.S. Pat. No. 5,478,732. Inulin can also be prepared by pressing processes known in the art such as are shown in U.S. Pat. No. 5,422,346.

The non-gelling and reduced viscosity property of the inulin, FOS and other dietary fiber components applicable to the present invention is to some extent directly related to the molecule size and thus the molecular weight of the particular polysaccharide. Inulin is a mixture of fructose polymers of varying chain lengths ranging from 2 to 60 monomers with a molecular weight of less than 11,000 and with a typical molecular weight of about 5,000. Fructooligosaccharides with chain lengths ranging from 2 to 8 fructose monomers have a molecular weight of less than about 1,500. The molecular weight of currently available dietary fibers typically exceed 100,000. For example, the molecular weight of guar is greater than 200,000, the molecular weight of tragacanth exceeds 800,000, and the molecular weight of pectin ranges from 40,000 to 400,000. The molecular weight of the low viscosity fiber component molecules in accordance with the present invention is preferably less than 40,000, more preferably less than 25,000 and most preferably less than about 5,000.

During hydration, a gram of either inulin or FOS binds less than two grams of water. In contrast, conventional dietary fiber components bind significant quantities of water. For example, one gram of xanthin will bind approximately 18.5 grams of water, one gram of carrageenan will bind approximately 32.9 grams of water, one gram of guar will bind approximately 24.9 grams of water, one gram of pectin will bind between 5 to 56.2 grams of water and one gram of karaya will bind approximately 12.5 grams of water. Accordingly, the water binding property of the low viscosity fiber component in accordance with the present invention is that one gram of the fiber component will preferably bind less than 10 grams of water, more preferably less than 5 grams of water and most preferable less than 3 grams of water.

Both the molecular weight property and the water absorbing capacity of a dietary fiber component are further related to the ability of that component to form a viscous solution when exposed to water. Typically, a 2% by weight H.sub.2O solution of tragacanth exhibits a viscosity of approximately 1,000 cps, a 2% by weight H.sub.2O solution of guar exhibits viscosity of about 25,000 cps, a 2% by weight H.sub.2O solution of karaya exhibits a viscosity of approximately 8,000 cps and a 2% by weight H.sub.2O solution of xanthin exhibits a viscosity of about 4,000 cps. In comparison, even a 10% by weight H.sub.2O solution of inulin and FOS exhibit relatively low viscosities on the order of about 2 cps. This is to be further compared with 10% by weight H.sub.2O solutions of native dietary fiber such as gum arabic, which exhibits a viscosity of about 20 cps, and arabinogalactan, which exhibits a viscosity of about 3 cps. Although arabic is a relatively large molecule with a molecular weight of up to 600,000, it is a globular rather than a linear molecule which resists hydration and thus exhibits a relatively low viscosity. The low viscosity fiber component in accordance with the present invention preferably comprises a component which when combined with water to form a 10% by weight H.sub.2O solution of such component exhibits a viscosity at 25.degree. C. of preferably less than 100, more preferably less than 25, and most preferably less than 5 cps.

The discussion of the preferred embodiment has been with respect to inulin and FOS which exhibit the desired properties of reduced viscosity in their natural, unprocessed form. However, the present invention also contemplates that various existing high molecular weight, nondigestible polysaccharides currently available as dietary fiber supplements may be processed to reduce their viscosity, gelling and other undesirable properties, and thus function in accordance with the present invention. Two examples are guar and various resistant starches.

Guar is a high molecular weight polysaccharide which at low concentrations forms viscous solution and gels. Prior art has shown, however, that through controlled hydrolysis, the average molecular weight of guar can be significantly reduced. This reduction in polymer size can significantly alter it viscosity building and gelling characteristics. For example, it is known that Taiyo Kagaku Co., Ltd produces a hydrolyzed guar through controlled enzymatic hydrolysis which produces an average molecular weight guar approximately one tenth that of the starting material. This hydrolysis improves the organoleptic properties of the resulting material and significantly reduces the viscosity and gelling characteristics. The viscosity of a solution of this hydrolyzed guar may be as much as 2,000 times or more lower than a similar solution of the native guar. Accordingly, it is contemplated that the low viscosity fiber component of the present invention, in addition to comprising inulin or FOS, may also comprise nondigestible polysaccharides which have been hydrolyzed or otherwise processed to reduce the viscosity of a solution of such material in accordance with the levels specified above.

Starch is a plant's storage form for glucose. Native dietary starch is a complex carbohydrate consisting of either straight (amylose: alpha-1,4 glucosidic bonds) or branched (amylopectin: alpha-1,4 and alpha-1,6 glucosidic bonds) chain monomers of glucose. For most of these complex polysaccharides, enzymatic hydrolysis occurs in the mouth, stomach and small intestines when ingested. Resistant starch is that fraction of dietary starch that escapes hydrolysis and enters the colon where it is subject to fermentation by the colonic flora. Accordingly, resistant starches are polysaccharides which are not digested by the human enzymes within the oral cavity and the gastrointestinal tract and thus are considered to be dietary fiber. Accordingly, it is contemplated that the non-gelling and low viscosity fiber component in accordance with the present invention may comprise resistant starches to the extent that the viscosity and other requirements described above are met.

Accordingly, the principle component of the dietary fiber supplement in accordance with the present invention is a non-gelling, low viscosity fiber component most commonly comprising a polysaccharide or complex carbohydrate exhibiting the properties described above.

One of the novel delivery forms of such tow viscosity fiber component is in a chewable form such as a chewable tablet which is capable of delivering supplemental quantities of dietary fibers from 0.5 to as much as 6.0 grams or more per dose. Preferably, the chewable tablet in accordance with the present invention is greater than 0.5 grams, more preferably greater than one gram and most preferably greater than two grams.

The manufacture of chewable tablets in accordance with the present invention utilizes tableting procedures and practices commonly known in the art and employed to produce tablets. Accordingly, the process of producing the chewable tablets in accordance with the present invention follows procedures known in the art. Further, except for the selection of the appropriate low viscosity fiber component, the formulation may be widely varied to attain the product attributes (flavor, aroma, color, texture and physical characteristics) and provide for appropriate and desired delivery of nutrients.

In general, the chewable tablet in accordance with the present invention is prepared by the dry blending of the desired ingredients to assure homogeneity in an appropriate blender (V, ribbon, paddle or plow), followed by compressing the mixture into a tablet possessing the preferred physical characteristics. To insure a final tablet of proper chewable consistency and/or facilitate tablet dissolution, etc., excipients such as microcrystalline cellulose, sugar alcohol (sorbitol, mannitol, xylitol) and sugars (glucose, fructose, sucrose) may be added either individually or in combination in any desired ratio. Further, to increase the nutritional value of the chewable tablet, the addition of various vitamins and/or minerals or combinations thereof may be included. These additives can increase the utility of the fiber supplement and be a particularly convenient mechanism for addressing a particular individual's nutritional needs. Still, further, to assure taste acceptability of the tablet, flavor additives, either individually or in combination, may be included. To improve the aesthetics of the tablets, the inclusion of coloring agents in any desired ratio may be used. Lubricants/release agents such as stearic acid, magnesium stearate or polyethylene glycol may also be included either individually or in combination to facilitate tablet ejection from the mold.

The tablet of the present invention can also include calcium so as to achieve the known benefits of the combination of calcium and dietary fiber.

Although it is contemplated that the chewable tablet in accordance with the present invention can be comprised almost exclusively (i.e. up to 99% or 100%) of the low viscosity fiber component, it is more likely that one or more of the above or other additives may be included to meet a particular nutritional, organoleptic or other goal. Accordingly, it is contemplated that the chewable tablet in accordance with the present invention will be comprised of at least about 10% by weight of the low viscosity component. More preferably, the chewable tablet is intended to comprise at least 30% by weight up to at least 50% by weight of the low viscosity component. Most preferably, the tablet comprises 30% to 60% by weight of the low viscosity fiber component.

The present invention further relates to methods of reducing serum cholesterol in humans. These methods comprise orally administering to a human in need of cholesterol reduction a safe and effective amount of a chewable tablet of the present invention. Preferably, the tablets are administered in 3-5 gram tablets 3-4 times daily.

In addition to providing the low viscosity fiber component as a chewable tablet, it is also contemplated that the low viscosity fiber component may be administered in powder form to be added with water or other fluid and reconstituted prior to ingestion.

Having described the details of the low viscosity fiber component and its administration in the form of a chewable tablet, the following examples demonstrate the present invention. All ingredient percentages refer to a measurement by weight.

EXAMPLE 1

Chewable Dietary Fiber Supplement

Chewable tablets as a delivery system were prepared in the manner described above. The following example demonstrates a sugar free chewable tablet formulated with inulin as the chewable matrix.

1 Ingredient Percentage Inulin 0.9901 Mg Stearate 0.0099

Ingredients are dry mixed in an appropriate blender (V, ribbon, paddle, and plow) to assure homogeneity of the batch and then compressed into tablets. This mixture when compressed into tablets had a pleasant, slightly sweet taste. The chewiness which is a function of the rate of hydration in the oral cavity can be somewhat controlled by the compression pressure. The shape, size, and weight of the tablet will vary to reflect the desired amount of fiber to be delivered. Above 10 grams the size may become overwhelming and the preferred shape may be cubular for these supplements with such large quantities of dietary fibers.

EXAMPLE 2

Chewable Tablet Formulated with Inulin

Chewable tablets as a delivery system were prepared in the manner described above. The following example demonstrates a sugar free chewable tablet formulated with inulin as the chewable matrix.

2 Ingredient Percentage Inulin 0.5935 Sorbitol 0.3956 Mg Stearate 0.0059 Spearmint flavor 0.0050

Ingredients are dry mixed in an appropriate blender (V, ribbon, paddle, and plow) to assure homogeneity of the batch and then compressed into tablets of appropriate size for the deliver of desired quantity of dietary fiber. A 5.055 gram tablet has been found to be a particularity pleasant way of delivering 3 grams of inulin.

EXAMPLE 3

Chewable Tablet—Formulated with FOS

Chewable tablets as a delivery system were prepared in the manner described above. The following example demonstrates a sugar free chewable tablet formulated with FOS as the chewable matrix.

3 Ingredient Percentage FOS 0.5935 Sorbitol 0.3956 Mg Stearate 0.0059 Orange flavor 0.0050

Ingredients are dry mixed in an appropriate blender (V, ribbon, paddle, and plow) to assure homogeneity of the batch and then compressed into tablets of appropriate size for the delivery of desired quantity of dietary fiber.

EXAMPLE 4

Chewable Tablet—Inulin & FOS

Chewable tablets as a delivery system were prepared in the manner described above. The following example demonstrates a sugar free chewable tablet formulated with a mixture of inulin and FOS as the chewable matrix.

4 Ingredient Percentage Inulin 0.2967 FOS 0.2967 Sorbitol 0.3956 Mg Stearate 0.0060 Orange favor 1.0000

Ingredients are dry mixed in an appropriate blender (V, ribbon, paddle, and plow) to assure homogeneity of the batch and then compressed into tablets of appropriate size for the delivery of desired quantity of dietary fiber.

EXAMPLE 5

Chewable Tablet—Vitamin & Mineral Fortified

The inclusion of vitamins and/or minerals either singly or in combination as a value added feature for chewable fiber tablets as a delivery systems for soluble dietary fiber or resistant starches. The tablets were prepared in the manner described above. The following example demonstrates a sugar-free, nutrient fortified chewable tablet.

5 Ingredient Percentage Inulin 0.5935 Sorbitol 0.2967 Mineral Premix 0.0692 Vitamin Premix 0.0297 Mg Stearate 0.0059 Spearmint flavor 0.0050

Ingredients are dry blended and then compressed into tablets of appropriate size and shape.

EXAMPLE 6

Chewable Tablet—Calcium Fortified

Chewable tablets as a delivery system were prepared in the manner described above. The following example demonstrates a sugar free chewable fiber tablet with the inclusion of a Calcium.

6 Ingredient Percentage Inulin 0.5935 Sorbitol 0.1978 Calcium Carbonate 0.1978 Calcium lactate Calcium gluconate, etc. Mg Stearate 0.0059 Butterscotch flavor 0.0050

Ingredients are dry blended and then compressed into tablets of appropriate weight and size. A 3.16 gram tablet of the above blend has been found to be a particular pleasant way of delivering 250 mg of calcium and 1.875 grams of inulin.

EXAMPLE 7

Chewable Tablet—with Added Bovine Immunoglobulin Concentrate (BIC)

The therapeutic value of the chewable fiber to the user tablet can be improved by the inclusion of biologics. Chewable fiber tablets as a delivery systems for bovine immunoglobulins were prepared in the manner described above. The following example demonstrates one such chewable tablet.

7 Ingredient Percentage Inulin 0.4926 Sorbitol 0.3284 BIC 0.1642 Mg Stearate 0.0098 Amaretto flavor 0.0048

Ingredients are dry blended and then compressed into tablets of appropriate size and weight.

The chewable dietary fiber supplemen-L can be used to deliver specific bovine antibodies to control the microbial flora in the oral cavity, stomach, small intestines, and colon. As such a chewable dietary fiber tablet with added bovine immunologlobulin can be used to reduce the occurrence of certain health concerns associated with microbial growth or as the therapy to treat these concerns.

The inclusion of other biologics is also contemplated. The chewable dietary fiber supplement provides a logical deli very system for a probiotic microbial mixture. The fermentable dietary fibers act as an enhancer of the probiotics cultures.

EXAMPLE 8

Chewable Tablet—Sugar-free

Chewable tablets as a delivery system were prepared in the manner described above. The following example demonstrates a sugar free chewable tablet.

8 Ingredient Percentage Inulin 0.7913 Sorbitol 0.1978 Mg Stearate 0.0059 Orange cream flavor 0.0050

Ingredients are dry blended and then compressed appropriate sized tablets. This mixture provides a particularly pleasant way of providing inulin in quantities between 500 mg and 8 grams.

EXAMPLE 9

Chewable Tablet—Containing Sugar

Chewable tablets as a delivery system were prepared in the manner described above. The following example demonstrates a sugar containing chewable tablet.

9 Ingredient Percentage Inulin 0.7913 Fructose 0.1978 Mg Stearate 0.0059 Orange cream flavor 1.0050

Ingredients are dry blended and then compressed into appropriate sized tablets. This mixture provides a particularly pleasant way of providing inulin in quantities between 500 mg and 8 grams.

Although the description of the preferred embodiment has been quite specific, it is contemplated that various modifications could be made without deviating from the spirit of the present invention. Accordingly, it is intended that the scope of the present invention be dictated by the appended claims rather than by the description of the preferred embodiment.

The invention claimed is:

1. A lozenge comprising, as a source of dietary fiber, a water-soluble, non-gelling dietary fiber component, wherein the dietary fiber component is selected from the group consisting of inulin, fructooligosaccharide, hydrolyzed guar, resistant starch, and a combination thereof, and is present in an amount of at least about 50% by weight of the lozenge, and wherein the dietary fiber component, when combined with water to form a 10% by weight solution, has a viscosity at 25° C. of less than 100 centipoise.

2. The lozenge of claim 1 wherein the lozenge is organoleptically pleasing.

3. The lozenge of claim 1 wherein the non-gelling dietary fiber solution has a viscosity at 25° C. of less than 25 centipoise.

4. A lozenge comprising, as a source of dietary fiber, a water-soluble, non-gelling dietary fiber component, wherein the dietary fiber component is selected from the group consisting of inulin, fructooligosaccharide, hydrolyzed guar, resistant starch, and a combination thereof, and is present in an amount of at least about 10% by weight of the lozenge, and wherein the dietary fiber component, when combined with water to form a 10% by weight solution, has a viscosity at 25° C. of less than 100 centipoise.

5. The lozenge of claim 4 wherein the non-gelling dietary fiber solution has a viscosity at 25° C. of less than 25 centipoise.

6. The lozenge of claim 4 wherein the lozenge is organoleptically pleasing.

7. The lozenge of claim 4, further comprising a component selected from the group consisting of vitamins, minerals, biologics, and a combination thereof.

8. The lozenge of claim 7 wherein the mineral is calcium.

9. The lozenge of claim 7 wherein the biologic is a probiotic microbial mixture.

10. The lozenge of claim 7 wherein the biologic is a probiotic culture.

11. The lozenge of claim 7 wherein the biologic is a bovine immunoglobulin concentrate.

12. The lozenge of claim 11 wherein the bovine immunoglobulin concentrate is selected from the group consisting of a colostrum, a hyper-immune colostrum, and a hyper-immune milk.

13. The lozenge of claim 7, wherein the biologic is an immunoglobulin.

14. The lozenge of claim 7 wherein the lozenge is organoleptically pleasing.

15. The lozenge of claim 7, wherein the dietary fiber component is present in an amount of at least about 20% by weight of the lozenge.

16. The lozenge of claim 7, wherein the dietary fiber component is present in an amount of at least about 30% by weight of the lozenge.

17. The lozenge of claim 7, wherein the dietary fiber component is present in an amount of at least about 40% by weight of the lozenge.

18. The lozenge of claim 7, wherein the dietary fiber component is present in an amount of at least about 45% by weight of the lozenge.

19. The lozenge of claim 7, wherein the dietary fiber component is present in an amount of at least about 50% by weight of the lozenge.

20. The lozenge of claim 4, further comprising a component selected from the group consisting of vitamins, minerals, biologics, and a combination thereof.

21. The lozenge of claim 20, wherein the dietary fiber component is present in an amount of at least about 20% by weight of the lozenge.

22. The lozenge of claim 20, wherein the dietary fiber component is present in an amount of at least about 30% by weight of the lozenge.

23. The lozenge of claim 20, wherein the dietary fiber component is present in an amount of at least about 40% by weight of the lozenge.

24. The lozenge of claim 20, wherein the dietary fiber component is present in an amount of at least about 45% by weight of the lozenge.

25. The lozenge of claim 20, wherein the dietary fiber component is present in an amount of at least about 50% by weight of the lozenge.

26. The lozenge of claim 4, wherein the dietary fiber component is present in an amount of at least about 20% by weight of the lozenge.

27. The lozenge of claim 4, wherein the dietary fiber component is present in an amount of at least about 30% by weight of the lozenge.

28. The lozenge of claim 4, wherein the dietary fiber component is present in an amount of at least about 45% by weight of the lozenge.

29. A lozenge comprising, as a source of dietary fiber, a water-soluble, non-gelling dietary fiber component, wherein the dietary fiber component is selected from the group consisting of inulin, fructooligosaccharide, hydrolyzed guar, resistant starch, and a combination thereof, and is present in an amount of at least about 40% by weight of the lozenge, and wherein the dietary fiber component, when combined with water to form a 10% by weight solution, has a viscosity at 25° C. of less than 100 centipoise.

* * * * *